United States Patent [19]

Thurn et al.

[11] 3,997,356
[45] Dec. 14, 1976

[54] REINFORCING ADDITIVE

[75] Inventors: Friedrich Thurn, Bruhl; Kurt Burmester, Overath-Steinenbruck; Johannes Pochert, Walberberg; Siegfried Wolff, Bruhl, all of Germany

[73] Assignee: Deutsche Gold- und Silber-Scheideanstalt vormals Roessler, Frankfurt, Germany

[22] Filed: Dec. 4, 1974

[21] Appl. No.: 529,568

Related U.S. Application Data

[62] Division of Ser. No. 415,176, Nov. 12, 1973, Pat. No. 3,876,489, and a continuation-in-part of Ser. No. 277,043, Aug. 1, 1972, Pat. No. 3,842,111.

[52] U.S. Cl. .................. 106/288 Q; 106/288 B; 106/308 Q
[51] Int. Cl.² .................................. C09C 1/28
[58] Field of Search ............ 106/288 Q, 308 Q; 260/448.8 R, 448.2 N

[56] References Cited
UNITED STATES PATENTS 3,768,537  10/1973  Hess et al. .................. 106/308 Q

*Primary Examiner*—Winston A. Douglas
*Assistant Examiner*—J. V. Howard
*Attorney, Agent, or Firm*—Cushman, Darby & Cushman

[57] ABSTRACT

Sulfur containing organosilicon compounds having the formula:

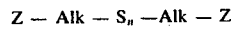

in which Z is:

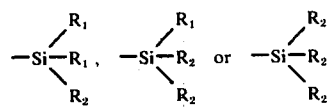

where $R_1$ is alkyl of 1 to 4 carbon atoms cyclohexyl or phenyl and $R_2$ is alkoxy of 1 to 8 carbon atoms, cycloalkoxy of 5 to 8 carbon atoms or alkylmercapto of 1 to 8 carbon atoms, alk of a divalent aliphatic hydrocarbon or unsaturated aliphatic hydrocarbon or a cyclic hydrocarbon containing 1 to 18 carbon atoms and $n$ is a whole number from 2 to 6 are used as reinforcing additives in rubber mixtures containing a silica or silicate filler, and in a given case carbon black; the organosilane is coated on the surface of the silica or silicate filler particles.

20 Claims, No Drawings

REINFORCING ADDITIVE

This application is a continuation-in-part of application Ser. No. 277,043, filed Aug. 1, 1972, now U.S. Pat. No. 3,842,111. This is a division of application Ser. No. 415,176 filed Nov. 12, 1973 now U.S. Pat. 3,876,489.

The present invention is directed to additives for silicate or silica filler containing rubber mixtures which additives favorably influence the production of the rubber mixtures and the properties of the vulcanizate in a surprising and decisive manner. These additives belong chemically to the group of organosilicon compounds containing sulfur in the molecule. The additives impart to the silica (or silicate) fillers improved reinforcing properties and increase the over-all cross-linking of the vulcanization; they are designated as reinforcing additives in the following description.

It is known that carbon blacks generally, and especially the especially developed types of carbon black, are not present merely as fillers in rubber vulcanizate but take part in a specific manner as reinforcing fillers (active fillers). The influence of carbon black on the reinforcement of the polymers and the determination of the rubber-filler-reciprocal effect are described for example in the magazine "Kautschuk und Gummi, Kunststoffe", No. 8, pages 470–474 (1966) and No. 1, pages 7–14 (1970).

The silica (or silicate) fillers, i.e., siliceous materials as, for example, highly dispersed silica, silicates or the like are known to be different in their activity from carbon blacks. This difference is recognized by two kinds of facts. First the reinforcing effect of silica or silicate fillers is different from that of carbon black because of their completely different type of surface. Secondly, the active silica influence the vulcanization process, especially if the vulcanization is effected by sulfur and accelerator additives. Previously there have been no sulfur vulcanizations in which the silica (or silicate) fillers did not reduce the cross-linking.

In recent years there have been attempts to improve the activity of silica (or silicate) fillers by admixing chemical substances to the starting mixture.

Thus it is known to use mercaptomethylalkoxysilane as an adhesive promoter between silicate materials such as glass, clay, asbestos and silica dioxide (silica) and organic resins such as butadiene-styrene copolymers, natural rubber, polyester resins, polystyrene and styrene-maleic anhydride-mixed polymers, whereby this silane is introduced on the substrate in any desired manner and bound with the resin, see German Offenlegungsschrift No. 2,038,715.

Furthermore, there are known organosiliconsulfide compounds having a sulfidic sulfur atom between the hydrocarbon radicals which are recommended for use as adhesive promoters or also as intermediate products for compounds which can be used as water repelling agents or oxidizing agents. The named organosilicon compounds, however, can also have sulfur containing end groups such as thiocyanato, xanthogenato, thioether, thionic acid ester groups or the like, see Lee, German Auslegeschrift 1,911,227.

The organo-organooxysilanes, for example, the 3-thiocyanatopropyl-trimethoxy- or triethoxysilane, which according to Belgian patent 770,097 and Rocktaschel U.S. application Ser. No. 163,467 filed July 16, 1971 now U.S. Pat. No. 3,798,196 find outstanding use in cross-linkable or vulcanizable mixtures of organic polymers, inorganic materials and the corresponding cross-linking or vulcanization agents or systems have similar end groups. The silanes described in German Auslegeschrift No. 1,911,227, Belgian Pat. No. 770,097 and the Rocktaschel U.S. application possess only a silicon atom bound to a carbon atom or a further silicon atom bound thereto by an oxygen atom or an amino nitrogen atom.

Furthermore there are known gamma-mercaptopropyltrimethoxy and triethoxy silanes as well as beta-mercaptoethyltriethoxy silane and other sulfur free silanes, which after subsequent partial hydrolysis and coating on the surface of silica or silicate filler particles serve to facilitate the workability of rubber mixtures and improvement of the strength properties of reinforced rubber articles, Vanderbilt U.S. Pat. No. 3,350,345.

Besides there are known tire threads produced from a rubber mixture which contain a silica as a filler and a silane as coupling agent, see Belgian Pat. No. 760,099. An exceedingly large number of silanes are included in the general formula in the Belgian patent, but from the introduction, the tables and examples there can only be found gamma-mercaptopropyltrimethoxysilane as the single coupling agent tried.

The present invention is drawn to a class of organosilanes containing sulfur in the molecule which are distinguished in several respects from the numerous known silanes in their outstanding advantages in use and especially in their suitability and reinforcing additives as is described and shown below. The new additives produce in siliceous fillers (i.e., silica and silicates) containing rubber mixtures and vulcanizates unforeseen, valuable and industrially outstanding properties, whereby the rubber mixtures contain at least one rubber, a cross-linking system (e.g., including sulfur), a sulfur containing organosilane, fillers and preferably further conventional rubber additives. The invention is characterized by the rubber mixture containing as a strengthening additive one or more organosilanes of the formula:

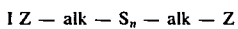

in which Z is:

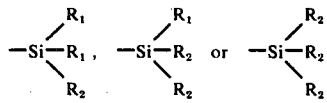

and in which $R_1$ is an alkyl group of 1 to 4 carbon atoms or phenyl and $R_2$ is an alkoxy group with 1 to 8, preferably 1 to 4, carbon atoms, a cycloalkoxy group with 5 to 8 carbon atoms or a straight or branched chain alkylmercapto group with 1 to 8 carbon atoms. All the $R_1$ and $R_2$ groups can be the same or different. Alk is a divalent hydrocarbon group with 1 to 18 carbon atoms. It can be straight or branched chain and can be a saturated aliphatic hydrocarbon group, an unsaturated aliphatic hydrocarbon group or a cyclic hydrocarbon group. Preferably alk has 1 to 6, most preferably 2 to 3 carbon atoms and $n$ is a [whole] number of 2 to 6, as well as one or more siliceous fillers (i.e. silica or a silicate), in a given case in admixture with carbon black. Preferably $n$ is 2 to 4, more preferably 3 to 4.

Preferably the rubber mixtures contain at least one organosilane, especially one or two, most preferably one, of formula I in which Z stands for the group

in which group $R_2$ is an alkyl group with 1 to 8 carbon atoms, preferably 1 to 4 carbon atoms and alk is a divalent straight chain saturated hydrocarbon radical (i.e., alkylene), having 1 to 6, preferably 2 or 3 carbon atoms. Besides the compounds named in the examples as preferred reinforcing additives, there can be used with advantage compounds of the formula

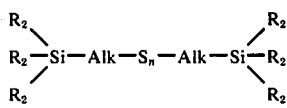

where $R_2$ is $OCH_3$; $-OCH_2CH_3$; $OCH_2CH_2CH_3$;

and $-OCH(CH_3)-CH_3$; Alk is $-CH_2CH_2-$; $-CH_2-\underset{CH_3}{CH}-$; $-CH_2CH_2CH_2-$;

$-CH_2-CH_2-\underset{CH_3}{CH}-$; $-CH_2CH_2CH_2CH_2-$; $-CH_2-\underset{CH_3}{CH}-CH_2-$; $-CH=CH-CH_2-$; $-CH_2-CH=CH-CH_2-$;

$-CH_2CH_2\underset{CH_3}{CH}CH_2-$; and $-CH_2CH_2CH_2-\underset{CH_3}{CH}-$; and n is 2.0 to 4.0

Other preferred silanes are those wherein in place of

in formula I, Z can be

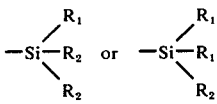

wherein $R_1$ is alkyl (branched or unbranched with 1 to 4 carbon atoms), phenyl or cyclohexyl and $R_2$ is as defined for formula II.

The new silanes used in the invention also have in the middle of the somewhat symmetrical molecule two or more connected sulfur atoms and two separated, to a certain degree, terminal standing silane groups. It must be accepted that this molecular structure causes the outstanding properties of the new vulcanization reinforcer.

The 3-mercaptopropyltrimethoxysilane already mentioned above in rubber mixtures which contain silica as a filler definitely increases the modulus values, tensile strength, abrasion resistance, rebound and shore hardness of the vulcanizate.

On the contrary, however, the scorch time and the Defo-elasticity of the unvulcanized mixtures are influenced unfavorably. The scorch times are shortened drastically. In the production of such mixtures even in the internal mixer frequently there occurs premature scorching which makes it impossible to further work the mixture.

The Defo-elasticity is sharply increased which means an increase of the elastic rubber portion in the crude mixture and makes more difficult the further processing, for example, by extrusion.

On the contrary, the rubber mixtures containing the new reinforcing additives employed in the present invention show definite industrial advantages in regard to the properties of the raw mixtures and the vulcanizates in comparison to those in the art. The raw mixtures now show especially a previously unknown degree of processing safety, a strongly reduced stiffness and only a slight increase of Defo-elasticity. All of these advantageous properties or effects for the first time open up the industrial use of such mixtures. The properties of the vulcanizates obtained are excellent and are comparable with the properties of correspondingly carbon black filled vulcanizates or even exceed these, as will be pointed out below. The mentioned improvement of the properties of the raw mixture and the vulcanizate for the first time opens field of use for silica fillers which previously were reserved for only carbon black as reinforcing filler.

The term "siliceous filler" is a broad term and refers to fillers which are rubber compatible or can be worked into rubber mixtures which fillers consist of silicates or silica, or contain silicates or silica and/or contain chemically bound silicates (or silica) in the widest sense, including mixtures of two or more siliceous fillers. Especially counted as siliceous fillers are:

Highly dispersed silica (silicon dioxide) having a specific surface area in the range of about 5 to 1000, preferably 20 to 400 $m^2/g$ (determined with gaseous nitrogen according to the known BET procedure) and with primary particle sizes in the range of about 10 to 400 nm. (nanometer, $10^{-9}$ meters), which can be produced, for example, by precipitation from solutions of silicates, by hydrolysis and/or oxidative high temperature conversion. There can also be used flame hydrolysis of volatile silicon halides, e.g., silicon tetrachloride, or by electric arc processes. These silicas, in a given case, can also be present as mixed oxides or oxide mixtures with oxides of the metals aluminum (alumina), magnesium (magnesium oxide), calcium (calcium oxide), barium (barium oxide), zinc (zinc oxide), zirconium (e.g., zirconium dioxide), or titanium (e.g., titanium dioxide).

Synthetic silicates, for example, aluminum silicate or alkaline earth silicates such as magnesium, or calcium silicate with specific surface areas of about 20 to 400 $m^2/g$ and primary particle sizes of about 10 to 400 nm.

Natural silicates, for example, kaolin, wollastonite, talc and asbestos as well as natural silicas, e.g., quartz or sand.

Glass fibers and glass fiber products such as mats, webs, strands, fabrics, non-woven fabrics and the like as well as microglass balls (microglass balloons).

The siliceous fillers mentioned can be added in amounts of about 10 or, in a given case, even less, up to about 250 parts by weight based on 100 parts by weight of rubber polymer.

As filler mixtures there can be used, for example, silica-kaolin or silica-glass fibers-asbestos, as well as blends of siliceous reinforcing fillers with the mentioned rubber blacks, for example, silica-ISAF carbon black or silica-glass fiber cords HAF carbon black.

Typical examples of siliceous fillers usable in the invention, for example, are those produced by Degussa, such as silica or silicates under the tradenames Aerosil, Ultrasil, Silteg, Durosil, Extrusil, Calsil, etc.

Furthermore there can be mixed into the rubber mixtures various additives which are well known in the rubber industry and widely used.

There are several advantages if the additive of the invention is not added as such to the rubber mixture but first a mixture of at least one siliceous filler and at least one organosilane of formula I above is prepared and this is then or later incorporated in the rubber mixture or the remaining components of the mixture of the rubber mixture in the customary manner with the help of conventional mixing apparatus and homogeneously distributed therein.

In the production of the master batch, there is still a fluid, dry product if there is mixed into the siliceous filler an equal or even larger amounts by weight of liquid organosilane. Consequently, it is also possible to add only a portion of the entire fillers needed to produce the rubber mixture which as a master batch already contains the entire amount of necessary silane.

Examples of organosilanes within formula I which can be used in the invention are bis[trialkoxysilyl-alkyl-(1)]-polysulfides such as bis[2-trimethoxy-, -triethoxy-, -tri-(methylethoxy)-, -tripropoxy-, -tributoxy and so forth up to -trioctyloxysilyl-ethyl]-polysulfides, namely the di-, tri-, tetra-, penta-, and hexasulfides, further the bis-[3-trimethoxy-, -triethoxy-, -tri-(methylethoxy)-, -tripropoxy-, -tributoxy- and so forth up to -trioctoxypropyl]- polysulfide, namely again the di-, tri-, tetra-, penta- and hexasulfide; furthermore the corresponding bis[3-trialkoxysilylisobutyl]- polysulfides, the corresponding bis[4-trialkoxysilyl-butyl]- polysulfides and so forth up to bis[6-trialkoxysilyl-hexyl]- polysulfides. Of those chosen, there are preferred relatively simply constructed organosilanes of formula I including bis-[3-trimethoxy-, -triethoxy-, and -tripropoxysilyl-propyl]- polysulfides namely the di-, tri- and tetrasulfides. These and the other organosilanes of formula I which can be added with good success can be made according to the process of Meyer-Simon application Ser. No. 277,043 filed on Aug. 1, 1973 which corresponds to German patent applications Nos. P 2,141,159.6; P 2,141,160.9 and P 2,212,239.9. The entire disclosure of Meyer-Simon (and the corresponding German applications) is hereby incorporated by reference. Typical examples of specific compounds within formula I which can be used in the invention include:

Examples of compounds within the invention include 3,3'-bis (trimethoxysilylpropyl) disulfide, 3,3'-bis (triethoxysilylpropyl) tetrasulfide, 3,3'-bis(trimethoxysilylpropyl) tetrasulfide, 2,2'-bis (triethoxysilylethyl) tetrasulfide, 3,3'-bis (trimethoxysilylpropyl) trisulfide, 3,3'-bis (triethoxysilylpropyl) trisulfide, 3,3'-bis (tributoxysilylpropyl) disulfide, 3,3'-bis(trimethoxysilylpropyl) hexasulfide, 3,3'-bis(trioctoxysilylpropyl) tetrasulfide, 3,3'-bis(trihexoxysilylpropyl) disulfide, 3,3'-bis(tri-2''-ethylhexoxysilylpropyl) trisulfide, 3,3'-bis(triisooctoxysilylpropyl) tetrasulfide, 3,3'-bis(tri-t-butoxysilylpropyl) disulfide, 2,2'-bis(methoxy diethoxy silyl ethyl)tetrasulfide, 2,2'-bis (tripropoxysilylethyl) pentasulfide, 3,3'-bis (tricyclohexoxysilylpropyl) tetrasulfide, 3,3'-bis(tricyclopentoxysilylpropyl) trisulfide, 2,2'-bis(tri-2''-methylcyclohexoxysilylethyl) tetrasulfide, bis(-trimethoxyxilylmethyl) tetrasulfide, 3,3'-bis (trimethylmercaptosilylpropyl) tetrasulfide, 2,2'-bis(triethylmercaptosilylethyl) disulfide, 2,2'-bis(tributylmercaptosilylethyl) trisulfide, 2,2'-bis(tri sec. butylmercaptosilylethyl) trisulfide, 3,3'-bis (trioctylmercaptosilylpropyl) tetrasulfide, 2,2'-bis (trihexylmercaptosilylethyl) hexasulfide, 3,3'-bis (ethyldipropylmercaptosilylpropyl) tetrasulfide, 3-methoxy ethoxy propoxysilyl 3'-diethoxybutoxysilylpropyltetrasulfide, 2,2'-bis (dimethyl methoxysilylethyl) disulfide, 2,2'-bis(dimethyl sec.butoxysilylethyl) trisulfide, 3,3'-bis (methyl butylethoxysilylpropyl) tetrasulfide, 3,3'-bis(-di-t-butylmethoxysilylpropyl) tetrasulfide, 2,2'-bis (phenyl methyl methoxysilylethyl) trisulfide, 3,3'-bis (diphenyl isopropoxysilylpropyl) tetrasulfide, 3,3'-bis(-diphenyl cyclohexoxysilylpropyl) disulfide, 3,3'-bis(-dimethyl ethylmercaptosilylpropyl) tetrasulfide, 2,2'-bis(methyl dimethoxysilylethyl) trisulfide, 2,2'-bis(-methyl ethoxypropoxysilylethyl) tetrasulfide, 3,3'-bis(-diethyl methoxysilylpropyl) tetrasulfide, 3,3'-bis (ethyl di-sec. butoxysilylpropyl) disulfide, 3,3'-bis(propyl diethoxysilylpropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3'-trimethoxysilylpropyl tetrasulfide, 4,4'-bis(trimethoxysilylbutyl) tetrasulfide, 6,6'-bis (triethoxysilylhexyl) tetrasulfide, 12,12'-bis(triisopropoxysilyl dodecyl) disulfide, 18,18'-bis(trimethoxysilyloctadecyl)tetrasulfide, 18,18'-bis (tripropoxysilyloctadecenyl) tetrasulfide, 4,4'-bis(trimethoxysilyl-buten-2-yl) tetrasulfide, 4,4'-bis (trimethoxysilylcyclohexylene) tetrasulfide, 5,5'-bis(dimethoxy methylsilylpentyl) trisulfide, 3,3'-bis(trimethoxysilyl-2-methyl propyl) tetrasulfide, 3,3'-bis(dimethoxyphenylsilyl-2-methylpropyl) disulfide.

The new silanes used in the invention can be added to the rubber mixture in amounts of 0.1 to 50 parts by weight, preferably within the limits of 0.5 to 25 parts by weight based on 100 parts by weight of rubber.

unless otherwise indicated all parts and percentages are by weight.

For use the organosilanes described above can be directly added to the rubber mixture or to the constituents of this mixture. Thereby it is not necessary and not advantageous to hydrolyze the organosilane before the addition.

However, the described organosilicon compounds can also be added to a part of the fillers, especially on the basis of their easy dosability and handling, whereby the liquid organosilane is converted into a powdery product and thus be used. In a given case, however, it is also possible, although not of special advantage, to uniformly coat the organosilane on the surface of the filler particles and in this form to carry out the use. All three or only two of the described methods of use can also be combined.

The rubber mixtures can be produced with one or more, in a given case oil-extended, natural and/or synthetic rubbers. These include especially natural rubber, synthetic rubbers, preferably diene elastomus as for example polybutadiene, polyisoprene, e.g., cis-polyisoprene, butadiene- styrene copolymer, butadiene-acrylonitrile copolymer, polymerized 2-chlorobutadiene, also butyl rubber, halogenated butyl rubber such as chlorinated butyl rubber, brominated butyl rubber as well as other known diene rubbers as for example terpolymers of ethylene, propylene and for example non-conjugated dienes and also non-conjugated polyenes, e.g., ethylene-propylene-cyclooctadiene, ethylene-propylene-norbornadiene, ethylene-propylene dicyclopentadiene and ethylene-propylene-cyclododecatriene. Also there can be used trans-polypentenamer, carboxy or epoxy rubbers and the like known elastomers. The chemical derivatives of natural rubber and modified natural rubber can also be used in the invention.

There can be added, in a given case, to the rubber mixtures of the organic polymers, the cross-linking system, the siliceous fillers and the organosilane additive known reaction accelerators, as well as one or more compounds of the group of antiaging agents, heat stabilizers, light stabilizers, ozone stabilizers, processing aids, plasticizers, tackifier, propellants, dyestuffs, pigments, waxes, extenders such as for example sawdusts, organic acids as for example stearic acid, benzoic acid, or salicyclic acid, additionally lead oxide or zinc oxide, activators such as for example triethanolamine, polyethylene glycol or hexanetriol-1,2,6, which are collectively known in the rubber industry. For the vulcanization the rubber mixture is generally mixed with cross-linking agents such as especially peroxides, e.g., benzoyl peroxide, sulfur or in special cases magnesium oxide, as well as in a given case vulcanization accelerators or mixtures of these.

The production of rubber mixtures as well as molding and vulcanization is carried out according to customary procedures in the rubber industry.

Industrial fields of use for the described rubber mixtures for examples are:

Industrial rubber articles such as cable insulation, hoses, driving belts, V-belts, conveyor belts, roller coating, vehicle tire treads, especially PKW and LKW-tire treads, as well as tire carcasses and tire sidewalls, cross country tires, shoe sole materials, packing rings, damping elements and many others. The new rubber mixtures have also been tested for glass fiber-adhesive mixtures and the like.

The filler Ultrasil VN2 is a precipitated active silica having a specific surface area (measured according to BET) of 130 m²/g and an average primary particle size of 28 nm.

The Ultrasil VN3 is likewise a precipitated active silica but has a specific surface area of 210 m²/g and an average primary particle size of 18 nm.

The rubber Buna CB10 is a polybutadiene rubber having a high cis-1,4- content.

Russ Corax 6LM is a ISAF-active carbon black wherein the large characters LM is an abbreviation for "Low Modulus".

Without limiting the invention the results are given in the following individual recipes for the new rubber mixtures with test results on the vulcanizates and evaluations or comparisons of these results. Therein many different concepts are repeated so that abbreviations can be used.

Definitions of the Abbreviations Used

| Abbreviation | Designation | Measured |
|---|---|---|
| DH | Defo hardness | grams (g) |
| DE | Defo elasticity | — |
| $t_s$ | Mooney-scorch time | minutes |
| $t_{35}$ | Mooney-cure time | minutes |
| ML 4 | Mooney plasticity at 100° C, standard rotor, testing time: 4 minutes | — |
| sp. gr. | Specific gravity | g/cm³ |
| VZ | Vulcanization time | minutes |
| VT | Vulcanization temperature | ° C. |
| ZF | Tensile strength | kp/cm² (kgf/cm²) |
| M(300, 200) | Modulus | kp/cm² (kgf/cm²) |
| BD | Elongation at break | % |
| bl.D. | Remaining elongation after break | % |
| E | Rebound | % |
| EF | Resistance to tear propagation | kp/cm (kgf/cm) |
| A | Abrasion (also "DIN abrasion") | mm³ |
| ΔT | Temperature increase (see Goodrich Flexometer) | ° C |

| (DIN = German industrial standards) | |
|---|---|
| Tensile strength, elongation at break and modulus on 6 mm large rings | DIN 53504 |
| Tear Propagation resistance | DIN 53507 |
| Rebound | DIN 53512 |
| Shore A hardness | DIN 53505 |
| Specific gravity | DIN 53550 |
| Mooney Test | DIN 53524 |
| Goodrich Flexometer (Determination of the heat build-up, ΔT | ASTM D 623-62 |
| Abrasion | DIN 53516 |

The vulcanizates were always produced in a steam heated multiple die press at the stated vulcanization temperatures.

In the examples, and elsewhere unless otherwise indicated all amounts of materials are always given in parts by weight.

Example 1

| Recipe: | Mixture 1 | Mixture 2 | Mixture 3 |
|---|---|---|---|
| Natural rubber (Ribbed Smoked Sheets I) | 100 | 100 | 100 |
| Pentachlorthiophenyl-zinc salt (Renacit IV of Farbenfabriken BAYER) | 0.25 | 0.25 | 0.25 |
| Finely divided precipitated silica (Ultrasil VN 3 of Degussa) | 40 | 40 | 40 |
| Zinc oxide | 3 | 3 | 3 |

Example 1-continued

| Recipe: | Mixture 1 | Mixture 2 | Mixture 3 |
|---|---|---|---|
| Stearic acid | 2 | 2 | 2 |
| 3-mercaptopropyltrimethoxy-silane | — | 2 | — |
| Bis-[3-trimethoxysilyl-propyl]-trisulfide | — | — | 2 |
| Dibenzothiazyldisulfide | 0.8 | 0.8 | 0.8 |
| Diphenylguanidine | 2.25 | 2.25 | 2.25 |
| Sulfur | 2.5 | 2.5 | 2.5 |

Mixing Procedure

Preliminary mixing was in a kneader at 80° C. flow temperature

| Additive or Treatment | Ended After |
|---|---|
| Natural rubber | 0 minutes |
| ½ the amount of silica | |
| stearic acid | |
| ½ the amount of silica | 1 minute |
| zinc oxide and organosilane | 2.5 minutes |
| Ram lifted and swept down | 4 minutes |
| Batch dumped | 4.5 minutes |

This mixture was allowed to be stored for 24 hours. Then the final mixing took place in the kneader at 80° C. flow temperature (Mixing Time 1.5 minutes).

Properties of the unvulcanized mixtures

| | Mixture 1 | Mixture 2 | Mixture 3 |
|---|---|---|---|
| DH/DE | 675/20 | precured (scorched) | 650/20 |
| $t_s$ | 6.4 | — | 5.0 |
| $t_{35}$ | 7.5 | — | 5.8 |
| ML 4 | 57 | 232 (increasing) | 54 |
| sp.gr. | 1.13 | 1.13 | 1.13 |

Properties of the vulcanized Mixture
Vulcanization temperature: 150° C.

| Mixture | | VZ | ZF | M 300 | BD | bl.D | E | SH | EF | A |
|---|---|---|---|---|---|---|---|---|---|---|
| 1 | 10 | 256 | 62 | 622 | 41 | 50 | 62 | 39 | | |
| | 20 | 250 | 58 | 630 | 43 | 47 | 64 | 31 | | |
| | 40 | 229 | 48 | 640 | 37 | 46 | 62 | 35 | 165 | |
| | 60 | 227 | 42 | 678 | 33 | 45 | 62 | 35 | | |
| 2 | 10 | | | | | | | | | |
| | 20 | | | | | | | | | |
| | 40 | | | | | | | | | |
| | 60 | | | | | | | | | |
| 3 | 10 | 274 | 95 | 558 | 41 | 47 | 63 | 27 | | |
| | 20 | 257 | 94 | 548 | 36 | 48 | 64 | 29 | | |
| | 40 | 262 | 84 | 580 | 35 | 48 | 61 | 25 | 140 | |
| | 60 | 242 | 76 | 582 | 28 | 47 | 61 | 27 | | |

Example 2

| Recipe: | Mixture 1 | Mixture 2 | Mixture 3 |
|---|---|---|---|
| cis-1,4-Polyisoprene rubber | 100 | 100 | 100 |
| finely divided, precipitated silica (ULTRASIL VN 3 of DEGUSSA) | 50 | 50 | 50 |
| Plasticizer (naphthenic hydrocarbons) | 3 | 3 | 3 |
| Zinc oxide (active) | 2 | 2 | 2 |
| Antioxidant (Mixture of aralkylated Phenols) | 1 | 1 | 1 |
| Mixture of equal parts of finely divided precipitated silica and hexanetriol (Aktivator R of DEGUSSA) | 4 | 4 | 4 |
| Benzoic acid | 0.8 | 0.8 | 0.8 |
| 3-Mercaptopropyl-trimethoxysilane | — | 1.5 | — |
| Bis-[3-triethoxysilyl-propyl]-tetrasulfide | — | — | 1.5 |
| Dibenzothiazyldisulfide | 0.8 | 0.8 | 0.8 |
| Diphenylguanidine | 1.6 | 1.6 | 1.6 |
| Sulfur | 2.5 | 2.5 | 2.5 |

Mixing Procedure

Premixing in a kneader at 80° C. flow temperature.

| Additive or Treatment | Ended After |
|---|---|
| cis-1,4-Polyisoprene rubber | 0 minutes |
| ½ amount of silica, stearic acid | |
| ½ amount of silica, plasticizer, zinc oxide, organosilane | 1 minute |
| | 2.5 minutes |
| Ram lifted and swept down | 4 minutes |
| Batch dumped | 4.5 minutes |

After standing for 24 hours final mixing was accomplished at 80° C. flow temperature in a kneader. (Mixing time 1.5 minutes).

Properties of the unvulcanized mixtures

| | Mixture 1 | Mixture 2 | Mixture 3 |
|---|---|---|---|
| DH/DE | 1500/6.0 | scorched | 1375/7.0 |
| $t_s$ | 9.2 | — | 6.5 |
| $t_{35}$ | 11.6 | — | 8.4 |
| ML 4 | 100 | 154 (increasing) | 91 |
| sp.gr. | 1.13 | 1.14 | 1.14 |

Properties of the vulcanized Mixture
Vulcanization temperature: 134° C.

| Mixture | | VZ | ZF | M 300 | BD | bl.D | E | SH | EF | A |
|---|---|---|---|---|---|---|---|---|---|---|
| 1 | 10 | 136 | 21 | 707 | 17 | 33 | 48 | 20 | | |
| | 20 | 198 | 27 | 742 | 24 | 36 | 59 | 30 | 196 | |
| | 30 | 215 | 31 | 733 | 30 | 36 | 61 | 28 | | |
| | 40 | 220 | 34 | 723 | 34 | 38 | 61 | 23 | | |
| 2 | 10 | | | | | | | | | |
| | 20 | | | | | | | | | |
| | 30 | | | | | | | | | |
| | 40 | | | | | | | | | |
| 3 | 10 | 199 | 47 | 632 | 23 | 40 | 63 | 40 | | |
| | 20 | 242 | 63 | 640 | 31 | 42 | 68 | 44 | 158 | |
| | 30 | 266 | 79 | 628 | 36 | 43 | 71 | 41 | | |
| | 40 | 272 | 87 | 620 | 41 | 44 | 72 | 43 | | |

In examples 1 and 2 there were used a rubber mixture based on natural rubber or synthetic cis-1,4-polyisoprene which contained as the siliceous filler a precipitated finely divided silica (Ultrasil VN 3 of Degussa). As reinforcing additive for the rubber mixture there were employed bis-[3-trimethoxysilyl propyl]-trisulfide or bis-[3-triethoxysilyl propyl]-tetrasulfide and 3-mercaptopropyl trimethoxysilane was employed as a comparison material of the prior art. As is already shown by the properties of the unvulcanized mixture in producing mixtures in the internal mixer only the raw rubber mixtures of the invention are able to be worked up further while the comparison mixtures could not be further worked because of the premature scorching.

The polysulfide organosilanes of the invention only shorten the scorching time $t_5$ and $t_{35}$ a short time in the mixtures and do not negatively effect the Mooney plasticity (ML 4) as well as the ratio DH/DE, if the mixtures with the organosilane additives are compared with the standard or reference mixtures.

The vulcanization properties of the new rubber mixtures are, compared to the silane free standard mixtures, are somewhat better in their resistance and clearly superior in regards to 300 Modulus, whereby the reinforcing effect which is produced by the invention is proven by numerical data. The named important advantages were produced by means of the added organosilane.

Mixture 3 of example 2 additionally also shows extraordinarily high tear propagation resistance values (tear propagation resistance).

Example 3

| Recipe: | Mixture 1 | Mixture 2 | Mixture 3 |
|---|---|---|---|
| Styrene-Butadiene-rubber (Buna Huls 1502) | 100 | 100 | 100 |
| Aluminumsilicate, precipitated (SILTEG AS 7 of DEGUSSA) | 40 | 40 | 40 |
| Zinc oxide (active) | 3 | 3 | 3 |
| Stearic acid | 1 | 1 | 1 |
| Cumaron resin (B ½ 85° C.) | 5 | 5 | 5 |
| Mixture of equal parts of finely divided precipitated silica and hexanetriol (Activator R of DEGUSSA) | 5 | 5 | 5 |
| Antioxidant (Mixture of aralkylated phenols) | 1 | 1 | 1 |
| 3-Mercaptopropyl-trimethoxysilane | — | 1.5 | — |
| Bis-[3-triethoxysilyl-propyl]-tetrasulfide | — | — | 1.5 |
| Benzothiazyl-2-cyclo-hexylsulfenamide | 0.4 | 0.4 | 0.4 |
| Diphenylguanidine | 0.8 | 0.8 | 0.8 |
| Sulfur | 2.0 | 2.0 | 2.0 |

Mixing Procedure

Premixing in a kneader at 80° C. flow temperature.

| Additive or Treatment | Ended after |
|---|---|
| Polymer (SBR) | 0 minutes |
| ½ amount of aluminum silicate, stearic acid, antioxidant | 1 minute |
| ½ amount of aluminum silicate, plasticizer, zinc oxide, organosilane, remaining chemicals | 2.5 minutes |
| Ram lifted and swept down | 4 minutes |
| Batch dumped | 4.5 minutes |

Accelerator and sulfur were mixed in on the rolls (Mixing time 1.5 minutes).

| Properties of the unvulcanized mixtures | | | |
|---|---|---|---|
| | Mixture 1 | Mixture 2 | Mixture 3 |
| $t_5$ | 4.9 | — | 3.1 |
| $t_{35}$ | 5.9 | — | 4.3 |
| ML 4 | 78 | 196 (increasing) | 82 |
| sp. gr. | 1.16 | 1.16 | 1.16 |

| Properties of vulcanized mixtures | | | | | | | | | |
|---|---|---|---|---|---|---|---|---|---|
| Vulcanization temperature: 150° C. | | | | | | | | | |
| Mixture | VZ | ZF | M 300 | BD | bl.D | E | SH | EF | A |
| 1 | 8 | 127 | 39 | 610 | 19 | 47 | 58 | 5 | |
| | 10 | 140 | 40 | 630 | 21 | 47 | 58 | 4 | |
| | 15 | 146 | 41 | 690 | 18 | 47 | 58 | 5 | 160 |
| | 20 | 121 | 41 | 583 | 16 | 47 | 58 | 4 | |
| 2 | 8 | | | | | | | | |
| | 10 | | | | | | | | |
| | 15 | | | | | | | | |
| | 20 | | | | | | | | |
| 3 | 8 | 142 | 78 | 560 | 15 | 50 | 59 | 6 | |
| | 10 | 140 | 69 | 528 | 13 | 50 | 59 | 5 | |
| | 15 | 130 | 71 | 465 | 11 | 51 | 60 | 4 | 132 |
| | 20 | 121 | 72 | 500 | 13 | 51 | 60 | 5 | |

Example 4

| Recipe: | Mixture 1 | Mixture 2 | Mixture 3 |
|---|---|---|---|
| Styrene-Butadiene-rubber (Buna Huls 1502) | 100 | 100 | 100 |
| Finely divided, precipitated silica (ULTRASIL VN 3 of DEGUSSA) | 50 | 50 | 50 |
| Zinc oxide (active) | 1 | 1 | 1 |
| Stearic acid | 2 | 2 | 2 |
| Antioxidant (mixture of aralkylated phenols) | 1 | 1 | 1 |
| Polyethylene glycol, molecular wt. 4000 (PEG 4000) | 2 | 2 | 2 |
| 3-mercaptopropyl-trimethoxysilane | — | 2 | — |
| Bis-[3-trimethoxysilyl-propyl]-disulfide | — | — | 2 |
| Dibenzothiazyldisulfide | 1 | 1 | 1 |
| Diphenylguanidine | 2 | 2 | 2 |
| Sulfur | 2 | 2 | 2 |

Mixing Procedure

Premixing in a kneader at 80° C. flow temperature.

| Additive or Treatment | Ended After |
|---|---|
| Polymer (SBR) | 0 minutes |
| ½ amount of silica, stearic acid, antioxidant | 1 minute |
| ½ amount of silica, zinc oxide, organosilane, other | 2.5 minutes |
| Ram lifted and swept down | 4 minutes |
| Batch dumped | 4.5 minutes |

After 24 hours storage the mixing in the kneader at 80° C flow through temperature was completed (Mixing time 1.5 minutes).

| Properties of the unvulcanized mixtures | | | |
|---|---|---|---|
| | Mixture 1 | Mixture 2 | Mixture 3 |
| DH/DE | 2250/19.5 | scorched | 2050/31.0 |
| $t_5$ | 8.1 | — | 7.8 |
| $t_{35}$ | 10.0 | — | 9.6 |
| ML 4 | 143 | 242 (increasing) | 116 |
| sp. gr. | 1.16 | 1.16 | 1.17 |

| Properties of the vulcanized mixtures | | | | | | | | | |
|---|---|---|---|---|---|---|---|---|---|
| Vulcanization temperature: 150° C. | | | | | | | | | |
| Mixture | VZ | ZF | M 300 | BD | bl.D | E | SH | EF | A |
| 1 | 5 | 170 | 40 | 660 | 40 | 33 | 71 | 17 | |
| | 10 | 174 | 42 | 640 | 34 | 33 | 72 | 14 | |
| | 15 | 178 | 41 | 625 | 31 | 33 | 71 | 13 | 126 |

Properties of the vulcanized mixtures
Vulcanization temperature: 150° C.

| Mixture | VZ | ZF | M 300 | BD | bl.D | E | SH | EF | A |
|---|---|---|---|---|---|---|---|---|---|
| | 20 | 196 | 42 | 647 | 32 | 33 | 71 | 14 | |
| 2 | 5 | | | | | | | | |
| | 10 | | | | | | | | |
| | 15 | | | | | | | | |
| | 20 | | | | | | | | |
| 3 | 5 | 208 | 63 | 592 | 33 | 32 | 70 | 17 | |
| | 10 | 222 | 77 | 548 | 29 | 32 | 71 | 13 | |
| | 15 | 222 | 85 | 523 | 24 | 32 | 70 | 14 | 89 |
| | 20 | 216 | 85 | 513 | 21 | 32 | 71 | 13 | |

Example 5

| Recipe: | Mixture 1 | Mixture 2 | Mixture 3 |
|---|---|---|---|
| Styrene-Butadiene-rubber (Buna Huls 1500) | 100 | 100 | 100 |
| Colloidalkaolin | 75 | 75 | 75 |
| Zinc oxide | 4 | 4 | 4 |
| Stearic acid | 2 | 2 | 2 |
| 3-mercaptopropyl-trimethoxysilane | — | 2.5 | — |
| Bis-[3-triethoxysilyl-propyl]-tetrasulfide | — | — | 2.5 |
| Dibenzothiazyldisulfide | 1.2 | 1.2 | 1.2 |
| Diphenylguanidine | 1.2 | 1.2 | 1.2 |
| Sulfur | 2.75 | 2.75 | 2.75 |

Mixing Procedure

Premixing in a kneader at 80° C. flow temperature.

| Additive or Treatment | Ended After |
|---|---|
| Rubber | 0 minutes |
| ½ amount of Kaolin, zinc oxide, organosilane | 2.5 minutes |
| Ram lifted and swept down | 4 minutes |
| Batch dumped | 4.5 minutes |

After 24 hours storage the mixing in the kneader at 80° C. flow through temperature was completed (Mixing time 1.5 minutes).

Properties of the unvulcanized mixtures

| | Mixture 1 | Mixture 2 | Mixture 3 |
|---|---|---|---|
| DH/DE | 1750/27 | 2550/32.5 | 1450/23.5 |
| $t_5$ | 34.0 | 6.6 | 29.2 |
| $t_{35}$ | 41.3 | 11.6 | 38.2 |
| ML 4 | 63 | 80 | 61 |
| sp. gr. | 1.32 | 1.32 | 1.32 |

Properties of the vulcanized mixtures
Vulcanization temperature: 150° C.

| Mixture | VZ | ZF | M 300 | BD | bl.D | E | SH | EF | A |
|---|---|---|---|---|---|---|---|---|---|
| 1 | 15 | 101 | 50 | 635 | 53 | 45 | 64 | 13 | |
| | 30 | 99 | 66 | 483 | 36 | 42 | 67 | 6 | |
| | 45 | 96 | 65 | 490 | 34 | 40 | 66 | 6 | 268 |
| | 60 | 94 | 64 | 480 | 34 | 40 | 67 | 9 | |
| 2 | 15 | 154 | 137 | 335 | 18 | 45 | 67 | 8 | |
| | 30 | 146 | 138 | 307 | 13 | 44 | 68 | 5 | |
| | 45 | 145 | 138 | 305 | 10 | 43 | 68 | 5 | 210 |
| | 60 | 147 | 143 | 303 | 11 | 42 | 67 | 5 | |
| | | | M 200 | | | | | | |
| 3 | 15 | 125 | 77 | 440 | 22 | 42 | 66 | 8 | |
| | 30 | 125 | 101 | 287 | 14 | 41 | 69 | 5 | |
| | 45 | 125 | 102 | 262 | 10 | 40 | 69 | 5 | 223 |
| | 60 | 129 | 104 | 293 | 14 | 39 | 69 | 4 | |

In examples 3 to 5 there were used rubber mixtures based on styrene-butadiene copolymers which contained as silicious fillers synthetic aluminum silicate or precipitated silica or a natural silicate (colloidal kaolin). As organosilane reinforcing additives there were employed bis-[3-triethoxysilyl propyl]-tetrasulfide or bis-[3-trimethoxysilyl propyl]-disulfide; these were compared with the 3-mercaptopropyl trimethoxysilane of the prior art in otherwise identical mixtures.

According to examples 3 and 4 it was not possible to produce kneader mixtures with 3-mercaptopropyl trimethoxysilane without premature scorching while this presents no problem wih the rubber mixtures containing the polysulfideorganosilanes of the invention.

In comparison with the respective standard mixtures without silane additive the vulcanization properties of the new rubber mixtures are clearly better. Tensile strength and modulus are increased, the remaining elongation after break was reduced and the DIN abrasion improved.

Example 5 shows that this effect occurs even in the addition of a relatively inactive silicate filler such as colloidal kaolin.

Example 5 also demonstrates with reference to the properties of the unvulcanized mixtures the clear advance of the present invention over the prior art compound 3-mercaptopropyl trimethoxysilane in that the prior art compound increases the values for DH/DE and ML 4 and it drastically shortens the scorch time $t_5$. On the contrary in the new rubber mixtures the values DH/DE and ML 4 are changed in a positive direction while the Mooney-scorch time $t_5$ is not substantially different from that of the comparison mixture without any silane additive.

The following examples 6 to 9 illustrate the fact that the new rubber mixtures also can be produced with equally good success based on butadiene acrylonitrile copolymers, butyl rubber, polychloroprene rubber or ethylenepropylene-terpolymer.

Example 6

| Recipe: | Mixture 1 | Mixture 2 |
|---|---|---|
| Butadiene-acrylonitrile-rubber (Perbunan N 3310 of Farbenfabriken Bayer AG) | 100 | 100 |
| Pyrogenic silica (Aerosil 130 V of DEGUSSA | 40 | 40 |
| Zinc oxide | 4 | 4 |
| Bis-[3-triethoxysilyl-propyl]-tetrasulfide | — | 1.5 |
| Dibenzothiazyldisulfide | 1.5 | 1.5 |
| Diphenylguanidine | 1.5 | 1.5 |
| Sulfur | 2.75 | 2.75 |

Mixing Procedure

Premixing in a kneader at 80° C. flow temperature.

| Additive or Treatment | Ended After |
|---|---|
| Butadiene-acrylonitrile-rubber | 0 minutes |
| ½ amount of silica, stearic acid | 1 minute |
| ½ amount of silica, zinc oxide, organosilane | 2.5 minutes |
| Ram lifted and swept down | 4 minutes |
| Batch dumped | 4.5 minutes |

After 24 hours storage the mixing in the kneader at 80° C. flow through temperature was completed (Mixing time 1.5).

Properties of the unvulcanized mixtures

|  | Mixture 1 | Mixture 2 |
|---|---|---|
| DH/DE | 2350/26 | 1950/31 |
| $t_s$ | 10.6 | 7.8 |
| $t_{35}$ | 13.4 | 9.8 |
| ML 4 | 132 | 105 |
| sp. gr. | 1.21 | 1.21 |

Properties of the vulcanized mixtures
Vulcanization temperature: 150° C.

| Mixture | VZ | ZF | M 200 | BD | bl.D. | E | SH | EF | A |
|---|---|---|---|---|---|---|---|---|---|
| 1 | 60 | 182 | 99 | 303 | 3 | 18 | 76 | 12 |  |
|  | 80 | 178 | 110 | 285 | 3 | 17 | 77 | 10 | 107 |
|  | 100 | 161 | 106 | 265 | 2 | 17 | 76 | 12 |  |
|  | 120 | 158 | 109 | 262 | 1 | 17 | 79 | 13 |  |
| 2 | 60 | 200 | 179 | 218 | 1 | 16 | 78 | 7 |  |
|  | 80 | 210 | 189 | 215 | 1 | 16 | 78 | 9 | 58 |
|  | 100 | 226 | 187 | 215 | 1 | 16 | 77 | 9 |  |
|  | 120 | 228 | 204 | 225 | 2 | 16 | 78 | 8 |  |

Example 7

| Recipe: | Mixture 1 | Mixture 2 |
|---|---|---|
| Butyl rubber | 100 | 100 |
| Finely divided, precipitated silica (ULTRASIL VN 3 of Degussa) | 50 | 50 |
| Zinc oxide | 5 | 5 |
| Stearic acid | 1 | 1 |
| Plasticizer (Petroleum oil) | 5 | 5 |
| Bis-[3-triethoxysilyl-propyl]-tetrasulfide | — | 1.5 |
| 2-Mercaptobenzothiazole | 1 | 1 |
| Tetramethylthiuramdisulfide | 0.5 | 0.5 |
| Sulfur | 1.5 | 1.5 |

Mixing Procedure

Premixing in the kneader at 60° C flow temperature.

| Additive or Treatment | Ended After |
|---|---|
| Butyl rubber | 0 minutes |
| ½ amount of silica, stearic acid | 2 minutes |
| ½ amount of silica, zinc oxide, organosilane, plasticizer | 4 minutes |
| Ram lifted and swept down | 6 minutes |
| Batch dumped | 7 minutes |

The final mixing took place on a open mill at 50° C. roll temperature.

| Additive or Treatment | Ended After |
|---|---|
| Batch charged | 0 minutes |
| Cut in twice right and left | 1 minute |
| Accelerator and sulfur | 2 minutes |
| Cut in twice right and left | 4 minutes |

-continued

| Additive or Treatment | Ended After |
|---|---|
| Mixture sheet pulled off | 5 minutes |

Properties of the unvulcanized mixtures

|  | Mixture 1 | Mixture 2 |
|---|---|---|
| DH/DE | 4300/3 | 3200/5 |
| $t_s$ | 1.2 | 2.9 |
| $t_{35}$ | 40 | 17.6 |
| ML 4 | 135 | 112 |
| sp. gr. | 1.15 | 1.15 |

Properties of the vulcanized mixtures
Vulcanization temperature: 160° C.

| Mixture | VZ | ZF | M 300 | BD | bl.D. | E | SH | EF | A |
|---|---|---|---|---|---|---|---|---|---|
| 1 | 10 | 85 | 19 | 893 | 100 | 12 | 64 | 15 |  |
|  | 20 | 103 | 23 | 850 | 100 | 13 | 67 | 16 |  |
|  | 40 | 117 | 27 | 818 | 100 | 13 | 68 | 23 |  |
|  | 60 | 116 | 28 | 795 | 96 | 13 | 70 | 25 | 270 |
|  | 80 | 112 | 28 | 778 | 93 | 13 | 70 | 26 |  |
| 2 | 10 | 108 | 27 | 805 | 97 | 11 | 63 | 17 |  |
|  | 20 | 133 | 34 | 773 | 78 | 11 | 64 | 22 |  |
|  | 40 | 145 | 40 | 738 | 68 | 12 | 67 | 23 |  |
|  | 60 | 148 | 43 | 708 | 64 | 12 | 69 | 28 | 227 |
|  | 80 | 151 | 45 | 693 | 63 | 12 | 69 | 27 |  |

Example 8

| Recipe: | Mixture 1 | Mixture 2 |
|---|---|---|
| Polychlorobutadiene rubber (Baypren 210 of Farbenfabriken Bayer AG, Leverkusen) | 100 | 100 |
| Di-o-tolylguanidine | 0.5 | 0.5 |
| Magnesiumoxide | 4 | 4 |
| Stearic acid | 1 | 1 |
| Mixture of liquid and plastic paraffins (Vaseline) | 1 | 1 |
| Phenyl-β-naphthylamine (antioxidant) | 2 | 2 |
| Finely divided, precipitated silica (ULTRASIL VN 2 of DEGUSSA) | 50 | 50 |
| Plasticizer (naphthenic hydrocarbons) | 10 | 10 |
| Bis-[3-triethoxysilyl-propyl]-tetrasulfide | — | 1.5 |
| 2-mercaptoimidazoline | 0.75 | 0.75 |
| Zinc oxide | 5 | 5 |

Mixing Procedure:

Premixing in the kneader at 60° C. flow temperature.

| Additive or Treatment | Ended After |
|---|---|
| Polychlorobutadiene, guanidine derivate, Antioxidant, magnesium oxide, Stearic acid, vaceline, ⅓ of the amount of the silica | 0 minutes |
|  | 1 minute |
| ⅓ of the amount of the silica, ½ the amount of the plasticizer, organosilane | 2.5 minutes |
| ⅓ the amount of the silica, ½ the amount of the plasticizer | |
| Ram lifted and swept down | 4 minutes |
| Removal and cooling 5 minutes in a waterbath | 5 minutes |

After 24 hours storage there was mixed in the kneader at 60° C flow temperature the 2-Merkaptoimidazoline and the zinc oxide and there was 5 minutes cooling in the waterbath.

Properties of the unvulcanized mixtures

|  | Mixture 1 | Mixture 2 |
|---|---|---|
| DH/DE |  |  |
| $t_s$ | 6.2 | 5.5 |
| $t_{35}$ | 10.8 | 10.1 |
| ML 4 | 91 | 84 |
| sp. gr. | 1.42 | 1.42 |

Properties of the vulcanized mixtures
Vulcanization temperature: 150° C.

| Mixture | VZ | ZF | M 300 | BD | bl.D. | E | SH | EF | A |
|---|---|---|---|---|---|---|---|---|---|
| 1 | 10 | 156 | 47 | 810 | 28 | 34 | 57 | 37 |  |
|  | 20 | 167 | 52 | 790 | 18 | 33 | 61 | 31 |  |
|  | 30 | 171 | 53 | 742 | 17 | 33 | 62 | 23 | 161 |
|  | 40 | 171 | 53 | 735 | 15 | 33 | 62 | 19 |  |
| 2 | 10 | 196 | 75 | 673 | 17 | 37 | 60 | 29 |  |
|  | 20 | 208 | 105 | 555 | 10 | 36 | 63 | 14 |  |
|  | 30 | 214 | 113 | 532 | 10 | 35 | 64 | 11 | 105 |
|  | 40 | 216 | 119 | 513 | 10 | 35 | 65 | 14 |  |

Example 9

| Recipe: | Mixture 1 | Mixture 2 |
|---|---|---|
| Terpolymer ethylene-propylene-rubber (Keltan 70 of DSM) | 100 | 100 |
| Finely divided, precipitated silica (EXTRUSIL of DEGUSSA) | 100 | 100 |
| Naphthenic hydrocarbon as plasticizer | 50 | 50 |
| Titandioxide | 10 | 10 |
| Zinc oxide | 5 | 5 |
| Stearic acid | 1 | 1 |
| Bis-[3-triethoxysilyl-propyl]-tetrasulfide | — | 5 |
| Tetramethylthiuramidisulfide | 0.8 | 0.8 |
| Dimethyldiphenylthiuramdisulfide | 1.5 | 1.5 |
| Telluriumdiethyldithiocarbamate | 0.8 | 0.8 |
| Dipentamethylenethiuramtetrasulfide | 0.8 | 0.8 |
| Sulfur | 2.0 | 2.0 |

Mixing Procedure

Premixing in the kneader at 80° C. flow temperature.

| Additive or Treatment | Ended After |
|---|---|
| Ethylene-Propylene-Terpolymer | 0 minutes |
| ½ amount of the silica, stearic acid | 1 minute |
| ½ amount of the silica, zinc oxide organosilane, remaining chemicals | 2.5 minutes |
| Ram lifted and swept down | 4 minutes |
| Batch dumped | 5 minutes |

After 24 hours storage the mixing was finished in the kneader at 80° C. flow temperature (Mixing time 1.5 minutes).

Properties of the unvulcanized mixtures

|  | Mixture 1 | Mixture 2 |
|---|---|---|
| DH/DE | 550/17.5 | 400/19.5 |
| $t_s$ | 8.5 | 19.2 |
| $t_{35}$ | 16.4 | 50.4 |
| ML 4 | 50 | 40 |
| sp. gr. | 1.16 | 1.16 |

Properties of the vulcanized mixtures
Vaulcanization temperature: 160° C.

| Mixture | VZ | ZF | M 300 | BD | bl.D. | E | SH | EF |
|---|---|---|---|---|---|---|---|---|
| 1 | 10 | 67 | 23 | 825 | 43 | 40 | 53 | 7 |
|  | 20 | 62 | 29 | 627 | 25 | 42 | 57 | 3 |
|  | 30 | 55 | 32 | 550 | 21 | 42 | 59 | 2 |
| 2 | 10 | 77 | 42 | 725 | 26 | 41 | 54 | 8 |
|  | 20 | 91 | 74 | 392 | 7 | 43 | 60 | 3 |
|  | 30 | 98 | 98 | 300 | 5 | 44 | 63 | 2 |

In example 6 there was used a rubber mixture formulated according to the invention based on a nitrile rubber which contained as the siliceous filler a pure silica produced by flame hydrolysis (Aerosil 130V of Degussa) and to which was added bis-[3-triethoxysilyl-propyl]-tetrasulfide as the organosilane reinforcing additive.

The Mooney viscosity of mixture 2 of Example 6 is clearly reduced in comparison to the standard mixture without organosilane addition. This signifies a reduced expenditure of energy and a lower cost in the further working of the raw mixture; the scorching time $t_5$ is only shortened unsubstantially. The vulcanizate of Mixture 2 shows a significant improvement in regard to tensile strength, modulus and DIN-abrasion when it is compared with comparison mixture 1 without organosilane addition.

According to example 7 the rubber mixture of the invention was based on butyl rubber containing a precipitated silica (Ultrasil VN 3 of Degussa) as the siliceous filler and the bis-[3-triethoxy-silyl propyl]-tetrasulfide as the organosilane reinforcing additive.

This addition of organosilane did not lead to premature scorching of the already very sharply accelerated standard mixture, but instead surprisingly to an increase in the Mooney-scorch time $t_5$. Tensile strength, modulus and remaining elongation of the vulcanizate were clearly better in comparison to the vulcanizate from the standard mixture.

Example 8 describes a rubber mixture based on a polychloroprene rubber with a precipitated silica (Ultrasil VN 3 of Degussa) as the siliceous filler and again using the bis-[3-triethoxysilyl propyl]-tetrasulfide as the organosilane reinforcer for cross-linking. The scorching behaviour of Mixture 2 is practically unchanged in comparison to the standard mixture, in regard to the Mooney viscosity Mixture 2 behaves somewhat more favourably. The properties of the vulcanizate of the rubber composition of the invention compared to those of the standard mixture are clearly superior. The tensile strength is more than 40 kp/cm² (40 kgf/cm²) and the 300% modulus at the same time more than 60 kp/cm² higher. The latter indicates an improvement of about 100% or more based on the Mixture 1 devoid of the organosilane.

Example 9 concerns a rubber mixture based on an ethylene-propylene nonconjugated diene-terpolymer with a further precipitated silica (Extrusil of Degussa) as the siliceous filler and the bis-[3-triethoxysilyl propyl]-tetrasulfide as the organosilane. Also in this case there is produced a surprising increase in the scorch time $t_5$; ML 4 is reduced about 10 Mooney units, both in comparison to the standard mixture without organosilane. The properties of the vulcanizate from Mixture 2 formulated according to the invention clearly exceed those of Mixture 1 without silane in regard to tensile strength, modulus and remaining elongation after break.

Example 10

| Passenger automobile - tire tread mixture Recipe | Mixture 1 | Mixture 2 |
|---|---|---|
| Oil extended styrene-butadiene rubber (Buna Huls 1712) | 96.5 | 96.5 |
| cis-1,4-Polybutadiene (Buna CB 10) | 30 | 30 |
| Finely divided precipitated silica (ULTRASIL VN 3 of DEGUSSA) | 75 | 70 |
| Bis-[3-triethoxysilyl-propyl]-tetrasulfide | 5 | — |
| Mixture of equal parts of precipitated silica (ULTRASIL VN 3) and Bis-[3-triethoxysilyl-propyl]-tetrasulfide | — | 10 |
| Zinc oxide | 4 | 4 |
| Stearic acid | 1.2 | 1.2 |
| Plasticizer (naphthenic hydrocarbons) | 15 | 15 |
| Antioxidant, phenyl-β-naphthylamine | 1.5 | 1.5 |
| Antioxidant, N-Iso-propyl-N-'-phenyl-p-phenylene-diamine | 1.5 | 1.5 |
| Benzthiazolyl-2-cyclohexylsulfenamide | 1.2 | 1.2 |
| Diphenylguanidine | 3.5 | 3.5 |
| Sulfur | 1.6 | 1.6 |

Mixing Procedure: "Up-side-down"

Premixing in the Kneader at 80° C. flow temperature

| Additive or Treatment | Ended-After |
|---|---|
| Step 1 | |
| Fillers, chemicals, polymers | 0 minutes |
| Ram lifted and swept down | 3 minutes |
| Batch dumped | 3.5 minutes |
| Storage | 24 hours |
| Step 2 | |
| Final mixing in the kneader at 80° C flow temperature. Accelerator and sulfur are mixed in in the kneader | |
| Mixing time | 1.5 minutes |

| Properties of the unvulcanized mixtures | Mixture 1 | Mixture 2 |
|---|---|---|
| $t_s$ | 20.0 | 18.1 |
| $t_{35}$ | 26.5 | 26.0 |
| ML 4 | 67 | 67 |
| sp. gr. | 1.19 | 1.19 |

Properties of the vulcanized mixtures
Vulcanization temperature: 160° C.

| Mixture | VZ | ZF | M 300 | BD | bl.D. | E | SH | EF | A |
|---|---|---|---|---|---|---|---|---|---|
| 1 | 20 | 190 | 66 | 592 | 26 | 38 | 64 | 23 | 91 |
| 2 | 20 | 196 | 63 | 627 | 26 | 38 | 62 | 27 | 90 |

Example 11

| "Earth-Mover" - Tire tread mixture Recipe: | Mixture 1 | Mixture 2 |
|---|---|---|
| Natural rubber (Ribbed Smoked Sheets I) | 100 | 100 |
| Pentachlorthiophenyl-zinc salt (Renacit IV of Farbenfabriken Bayer, Leverkusen) | 0.25 | 0.25 |
| ISAF-LM Carbon black (CORAX 6 LM of Degussa) | 60 | — |
| Mixture of 10 parts of bis[3-triethoxysilyl-propyl]-tetrasulfide and 100 parts of precipitated silica (ULTRASIL VN 3 of Degussa) | — | 66 |
| Zinc oxide | 5 | 5 |
| Stearic acid | 2.5 | 2.5 |
| Antioxidant, phenyl-α-naphthylamine | 1 | 1 |
| Antioxidant phenyl-β-naphthylamine | 1 | 1 |
| Antioxidant N-Isopropyl-N-phenyl-p-phenylendiamine | 0.8 | 0.8 |
| Rubber-ocozerite (Protektor 3888 of Luneburge Wachsbleiche, GmbH) | 0.8 | 0.8 |
| Plasticizer (naphthenic hydrocarbon) | 2 | 2 |
| Bis-[2-ethylamino-4-diethylamino-6-triazinyl]-disulfide | 0.6 | 0.6 |
| Diphenylguanidine | — | 2 |
| Sulfur | 1.2 | 1.2 |

| Additive or Treatment | Ended After |
|---|---|
| Step 1: | |
| Fillers, chemicals, polymer | 0 minutes |
| Ram lifted and swept down | 3 minutes |
| Batch dumped | 3.5 minutes |
| Storage time | 24 hours |
| Step 2: | |
| Final mixing in the kneader at 80° C. flow temperature. Accelerator and sulfur are mixed in in the kneader | |
| Mixing time | 1.5 minutes |

| Properties of the unvulcanized mixtures | Mixture 1 | Mixture 2 |
|---|---|---|
| Mooney Scorch $t_s$ | 25.4 | 19.9 |
| Mooney Cure $t_{35}$ | 28.1 | 25.3 |
| Mooney Viscosity ML 4 | 88 | 77 |
| sp.gr. | 1.15 | 1.18 |

Properties of the vulcanized mixtures
Vulcanization temperature: 145° C.

| Mixture | VZ | ZF | M 300 | BD | E | SH | EF | A | T (0.250″) |
|---|---|---|---|---|---|---|---|---|---|
| 1 | 60 | 249 | 139 | 490 | 36 | 68 | 31 | 102 | 87 |
| 2 | 60 | 257 | 119 | 547 | 41 | 76 | 42 | 104 | 64 |

According to Example 10 a passenger automobile tire tread (PKW) recipe and according to Example 11 an earth mover tire tread recipe are disclosed and used. As reinforcing additive for both recipes there were used bis-[3-triethoxysilylpropyl]-tetrasulfide, for the PKW tire tread in the form of a mixture with silica in the ratio 1:1 and for the earth mover tire tread in the form of a mixture with finely divided silica in the ratio 1:10.

Example 10 shows that the range of error of the rubber technique investigating methods used there was no difference between the application of the reinforcing additive in pure form and the application of the reinforcing additive in the form of a mixture with precipitated highly dispersed silica.

The properties of the vulcanized mixture containing silica and carbon black show clearly better values in tensile strength, rebound, resistance to tear propagation and heat build-up on dynamic stress than the vulcanized mixture containing only carbon black.

What is claimed is:

1. A composition suitable for use in a rubber mixture comprising 0.1 to 50 parts of an organosilane compound having the formula

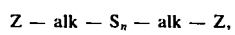

in which Z is

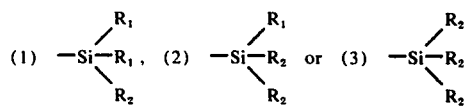

wherein $R_1$ is alkyl of 1 to 4 carbon atoms, cyclohexyl or phenyl and $R_2$ is alkoxy of 1 to 8 carbon atoms, cycloalkoxy with 5 to 8 carbon atoms or alkylmercapto with 1 to 8 carbon atoms, alk is a divalent hydrocarbon of 1 to 18 carbon atoms an n is a number of 3.0 to 6.0, and 10 to 250 parts of a siliceous filler.

2. A composition according to claim 1 wherein Alk is a saturated aliphatic hydrocarbon, unsaturated aliphatic hydrocarbon or cycloaliphatic hydrocarbon group.

3. A composition according to claim 2 wherein Alk has 1 to 6 carbon atoms.

4. A composition according to claim 3 wherein Alk is a saturated aliphatic hydrocarbon group of 2 to 4 carbon atoms and n is a number of 3.0 to 4.0.

5. A composition according to claim 2 wherein Z is (3).

6. A composition according to claim 5 wherein Alk has 1 to 6 carbon atoms and all $R_2$ groups are alkoxy of 1 to 4 carbon atoms.

7. A composition according to claim 5 wherein Alk is a saturated aliphatic hydrocarbon group of 2 to 3 carbon atoms.

8. A composition according to claim 7 wherein the siliceous material is silica, kaolin or aluminum silicate.

9. A composition according to claim 6 wherein the siliceous material is silica, kaolin or aluminum silicate.

10. A composition according to claim 9 wherein the siliceous material is silica.

11. A composition according to claim 10 wherein the silica is finely divided precipitated silica or pyrogenic silica.

12. A composition according to claim 11 wherein the organosilane compound is 3,3'-bis-[triethoxysilyl propyl]tetrasulfide.

13. A composition according to claim 1 wherein the organosilane has the formula

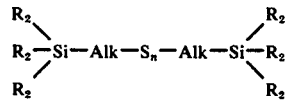

where $R_2$ is alkoxy of 1 to 3 carbon atoms, Alk is alkylene of 2 to 5 carbon atoms and n is 3.0 to 4.0.

14. A composition according to claim 1 wherein the organosilane is present as a surface coating on the siliceous filler.

15. A composition according to claim 1 consisting of the mixture of the siliceous filler and the organosilane.

16. A composition according to claim 1 where Z is (3), $R_2$ is ethoxy and alk is alkylene of 2 to 4 carbon atoms.

17. A composition according to claim 1 wherein the siliceous filler is kaolin.

18. A composition according to claim 1 wherein the siliceous filler is aluminum silicate.

19. A composition according to claim 1 consisting essentially of said organosilane and said siliceous filler.

20. A composition according to claim 1 consisting essentially of the mixture of the siliceous filler and the organosilane.

* * * * *

UNITED STATES PATENT OFFICE
CERTIFICATE OF CORRECTION

Patent No. 3,997,356           Dated December 14, 1976

Inventor(s) Friedrich THURN, Kurt BURMESTER, Johannes POCHERT and Siegfried WOLFF It is certified that error appears in the above-identified patent and that said Letters Patent are hereby corrected as shown below:

On the title page insert -

| [30] | August 17, 1971 | Germany | 2141159 |
|---|---|---|---|
| | August 17, 1971 | Germany | 2141160 |
| | March 14, 1972 | Germany | 2212239 |
| | November 13, 1972 | Germany | 2255577 |

On the title page Item (62) "3,876,489 should read -- 3,873,489 --.

Column 1, line 6, "3,876,489" should read -- 3,873,489 --.

Signed and Sealed this

Fifth Day of September 1978

[SEAL]

Attest:

RUTH C. MASON
*Attesting Officer*

DONALD W. BANNER
*Commissioner of Patents and Trademarks*